US010639443B2

(12) United States Patent
Avitsian et al.

(10) Patent No.: US 10,639,443 B2
(45) Date of Patent: *May 5, 2020

(54) REVERSIBLE AIRWAY DEVICE AND RELATED METHOD FOR VENTILATING A SUBJECT

(71) Applicant: THE CLEVELAND CLINIC FOUNDATION, Cleveland, OH (US)

(72) Inventors: Rafi Avitsian, Solon, OH (US); Andrew Zura, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/328,978

(22) PCT Filed: Jul. 24, 2015

(86) PCT No.: PCT/US2015/041870
§ 371 (c)(1),
(2) Date: Jan. 25, 2017

(87) PCT Pub. No.: WO2016/014879
PCT Pub. Date: Jan. 28, 2016

(65) Prior Publication Data
US 2017/0216545 A1 Aug. 3, 2017

Related U.S. Application Data

(63) Continuation-in-part of application No. 14/048,343, filed on Oct. 8, 2013.
(Continued)

(51) Int. Cl.
A61M 16/04 (2006.01)
A61B 1/267 (2006.01)
A61B 1/00 (2006.01)

(52) U.S. Cl.
CPC ..... *A61M 16/0488* (2013.01); *A61B 1/00135* (2013.01); *A61B 1/267* (2013.01);
(Continued)

(58) Field of Classification Search
CPC .......... A61M 16/0488; A61M 16/0475; A61M 16/0459; A61M 16/0486; A61M 16/0084;
(Continued)

(56) References Cited

U.S. PATENT DOCUMENTS 6,634,354 B2 * 10/2003 Christopher ...... A61M 16/0488
128/200.26
2001/0032646 A1 10/2001 Christopher
(Continued)

*Primary Examiner* — Timothy A Stanis
*Assistant Examiner* — Victoria Murphy
(74) *Attorney, Agent, or Firm* — Tarolli, Sundheim, Covell & Tummino LLP

(57) ABSTRACT

One aspect of the present disclosure relates to a reversible airway device for ventilating a subject. The airway device can comprise a laryngeal tube, an endotracheal tube, and a sealing mechanism. The laryngeal tube can include a tubular guide having a distal end portion, a proximal end portion, and a first passageway extending between the distal and proximal end portions. The laryngeal tube can further include axially spaced apart distal and proximal cuffs coupled thereto. The endotracheal tube can be slidably disposed within the first passageway. The endotracheal tube can have a second passageway that is disposed within the first passageway. The sealing mechanism can be disposed within the first passageway and configured to occlude the flow of gas through the first passageway.

20 Claims, 10 Drawing Sheets

Related U.S. Application Data

(60) Provisional application No. 62/028,886, filed on Jul. 25, 2014, provisional application No. 61/710,810, filed on Oct. 8, 2012.

(52) U.S. Cl.
CPC ........ *A61M 16/04* (2013.01); *A61M 16/0409* (2014.02); *A61M 16/0459* (2014.02); *A61M 16/0475* (2014.02); *A61M 16/0486* (2014.02); *A61M 16/0434* (2013.01)

(58) Field of Classification Search
CPC .............. A61M 16/04; A61M 16/0409; A61M 16/0415; A61M 16/0418; A61M 16/0434; A61M 16/0445; A61M 16/0493; A61M 16/06; A61M 16/08; A61B 1/00135; A61B 1/267
See application file for complete search history.

(56) References Cited

U.S. PATENT DOCUMENTS

| | | |
|---|---|---|
| 2005/0051175 A1 | 3/2005 | Brain |
| 2012/0234328 A1* | 9/2012 | Bertram ................ A61M 16/04 128/207.15 |
| 2013/0056003 A1 | 3/2013 | Miller et al. |
| 2014/0096766 A1 | 4/2014 | Avitsian et al. |

* cited by examiner

REVERSIBLE AIRWAY DEVICE AND RELATED METHOD FOR VENTILATING A SUBJECT

RELATED APPLICATIONS

This application is a 35 U.S.C. § 371 National Stage Patent Application of International PCT Application Serial No. PCT/US15/41870, having an international filing date of Jul. 24, 2015, which claims the benefit of U.S. Provisional Patent Application Ser. No. 62/028,886, filed Jul. 25, 2014. This application is also a continuation-in-part of U.S. patent application Ser. No. 14/048,343, filed Oct. 8, 2013, which claims the benefit of U.S. Provisional Patent Application Ser. No. 61/710,810, filed Oct. 8, 2012. The application claims priority to and incorporates by reference the above applications in their entirety for all purposes.

TECHNICAL FIELD

The present disclosure relates generally to the field of airway management, anesthesiology, and emergency medicine and, more particularly, to a reversible airway device and related method for ventilating a subject using the airway device that can convert supraglottic and infraglottic ventilation interchangeably and does not risk disconnection or loss of the patient's airway during ventilation.

BACKGROUND

Airway devices are widely used in hospital surgical environments to provide respiratory assistance and ventilate patents during medical procedures. While there are a multitude of airway devices currently on the market, one popular airway device is an endotracheal tube and another is a supra-glottic support device, such as a laryngeal tube. While the use of these devices is widespread, there are disadvantages associated with each of these devices.

Endotracheal tubes, for example, are used to ventilate patients requiring anesthesia and/or respiratory assistance. An example of a conventional endotracheal tube is a plastic tube, which is inserted into a subject's mouth, passed down the trachea through the vocal cords, and lodged in the trachea proximal (or above) the lungs. The endotracheal tube may have a cuff or balloon portion surrounding the circumference of the endotracheal tube near the distal end that rests in the subject's trachea. After the endotracheal tube has been inserted properly, the cuff may be inflated to seal against the wall of the trachea. Once sealed, positive pressure ventilation may be used to provide respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and the trachea wall and entering the subject's lungs.

In its basic (standard) version, the supraglottic laryngeal tube is made up of a tube with a larger balloon cuff in the middle (oropharyngeal cuff) and a smaller balloon cuff at the end (esophageal cuff). The tube is kinked at an angle of 30-45° in the middle, with the kink being located in the larger cuff. There are a number of openings in the anterior wall of the tube that are used for ventilating a patient. In some configurations, for example, there are two apertures located between the two cuffs, through which ventilation takes place. Both cuffs are inflated through a single small lumen line and pilot balloon. The cuffs are high-volume, low-pressure cuffs with inflating volume ranging from 10 ml (size 0) to 90 ml (size 5).

In patients that require ventilation with an airway device (e.g., critically ill or injured subjects), it is important to maintain a continuous airway. In such patients, if ventilation begins with a supra-glottic support device (e.g., a laryngeal tube) and intubation subsequently becomes necessary, the supra-glottic support device must be removed from the patient so that an endotracheal tube can be placed. Doing so, however, requires that the patient's airway be temporarily disrupted while also increasing the risk that the patient's airway may not be recovered. Additionally, placing an endotracheal tube requires the skill of an experienced medical professional, who may not be present in all circumstances in which unexpected intubation is required.

SUMMARY

The present disclosure relates generally to the field of airway management, anesthesiology, and emergency medicine and, more particularly, to a reversible airway device and related method for ventilating a subject using the airway device that can convert supraglottic and infraglottic ventilation interchangeably and does not risk disconnection or loss of the patient's airway during ventilation.

One aspect of the present disclosure relates to a reversible airway device for ventilating a subject. The airway device can comprise a laryngeal tube, an endotracheal tube, and a sealing mechanism. The laryngeal tube can include a tubular guide having a distal end portion, a proximal end portion, and a first passageway extending between the distal and proximal end portions. The laryngeal tube can further include axially spaced apart distal and proximal cuffs coupled thereto. The endotracheal tube can be slidably disposed within the first passageway. The endotracheal tube can have a second passageway that is disposed within the first passageway. The sealing mechanism can be disposed within the first passageway and configured to occlude the flow of gas through the first passageway.

Another aspect of the present disclosure relates to a method for providing an artificial airway in a subject. One step of the method can comprise providing a reversible airway device. The reversible airway device can comprise a laryngeal tube, an endotracheal tube, and a sealing mechanism. The laryngeal tube can include a tubular guide having a distal end portion, a proximal end portion, and a first passageway extending between the distal and proximal end portions. The laryngeal tube can further include axially spaced apart distal and proximal cuffs coupled thereto. The endotracheal tube can be slidably disposed within the first passageway. The endotracheal tube can have a second passageway that is disposed within the first passageway. The sealing mechanism can be disposed within the first passageway and configured to occlude the flow of gas through the first passageway. Next, the laryngeal tube can be inserted into the subject so that a first airtight seal is formed between the distal cuff and the proximal esophagus, and a second airtight seal is formed between the proximal cuff and the oropharynx. The endotracheal tube can then be deployed so that a distal end of the endotracheal tube is positioned below the vocal cords of the subject. The endotracheal tube can be retracted so that the distal end of the endotracheal tube is positioned above the vocal cords. A flow of gas through the second passageway can be uninterrupted during the inserting and deploying steps.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
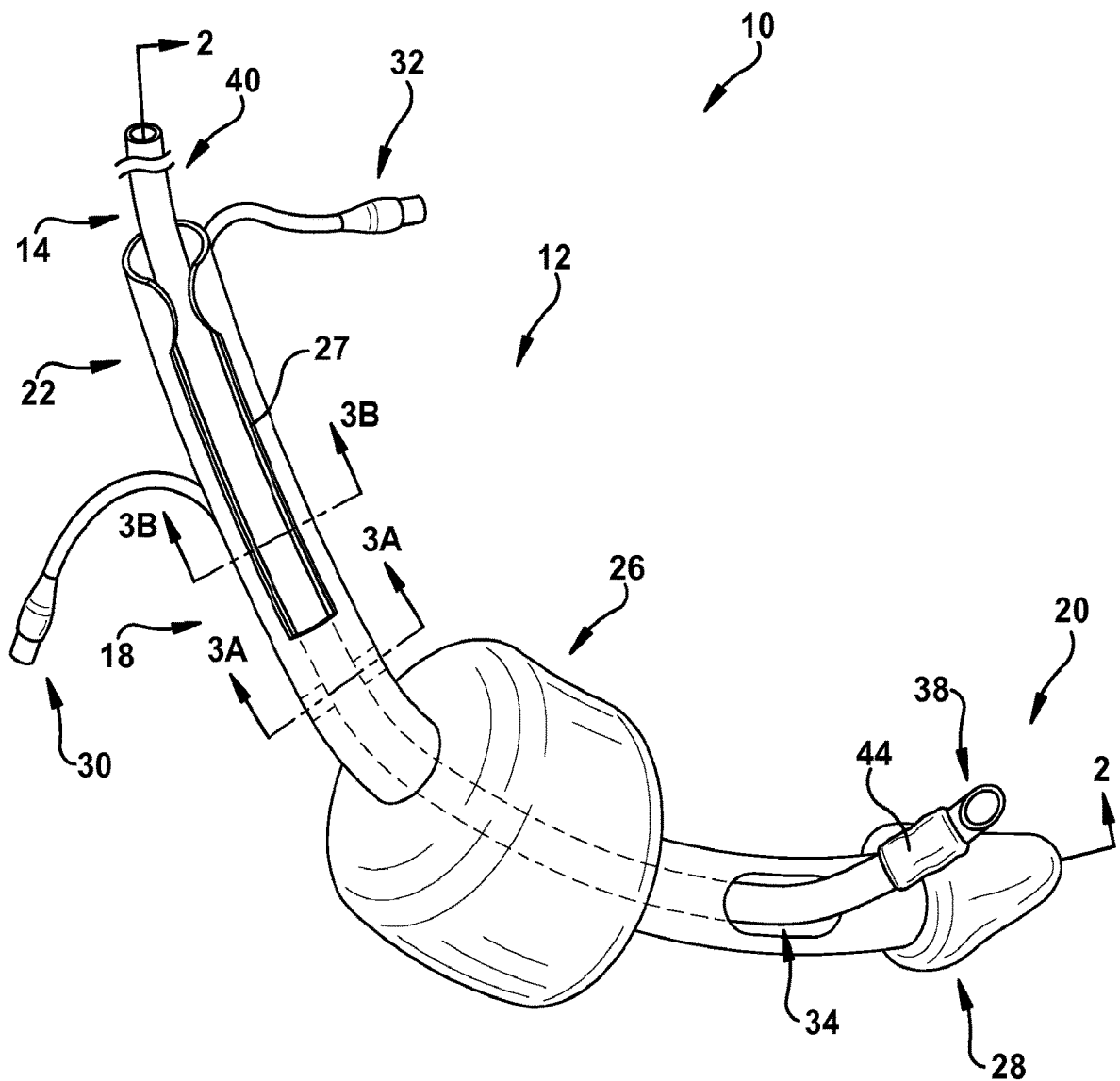
FIG. 1 is a perspective view of a reversible airway device constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, anesthesia, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure relates generally to the field of airway management, anesthesiology, and emergency medicine and, more particularly, to a reversible airway device and related method for ventilating a subject using the airway device that can convert supraglottic and infraglottic ventilation interchangeably and does not risk disconnection or loss of the patient's airway during ventilation. As representative of one aspect of the present disclosure, FIG. 1 illustrates a reversible airway device 10 for establishing an artificial airway and providing continuous ventilation in a subject when needed. Existing airway devices and associated methods for ventilating subjects involve the introduction of an endotracheal tube through a supra-glottic airway support device. This is time consuming, involves multiple devices, entails ventilation stoppage, and requires a high level of medical expertise. Advantageously, the present disclosure integrates both sub-glottic and supra-glottic support components that can easily and automatically provide intubation and, when needed, be quickly changed to function as a supra-glottic airway support while not compromising ventilation.

Reversible Airway Devices

One aspect of the present disclosure can include a reversible airway device 10. The reversible airway device 10 can generally include a supra-glottic airway support 12 (e.g., a laryngeal tube), an endotracheal tube 14, and a sealing mechanism 16. By "reversible", it is meant that an artificial airway provided by the supra-glottic airway support 12 can be readily exchanged for an artificial airway provided by the endotracheal tube 14 without removing or disconnecting any component(s) of the airway device 10, and while maintaining continuous, uninterrupted ventilation. In other words, the term "reversible" can refer to the ability of the airway device 10 to be automatically changed from a supra-glottic airway support 12 to an endotracheal tube 14, and then back to a supra-glottic airway support, without compromising ventilation. As discussed in more detail below, the airway device 10 of the present disclosure can be used for all indications of a supra-glottic airway support device where there is a possibility that endotracheal intubation may be necessitated (e.g., in trauma or critically ill patients).

Figure 2:
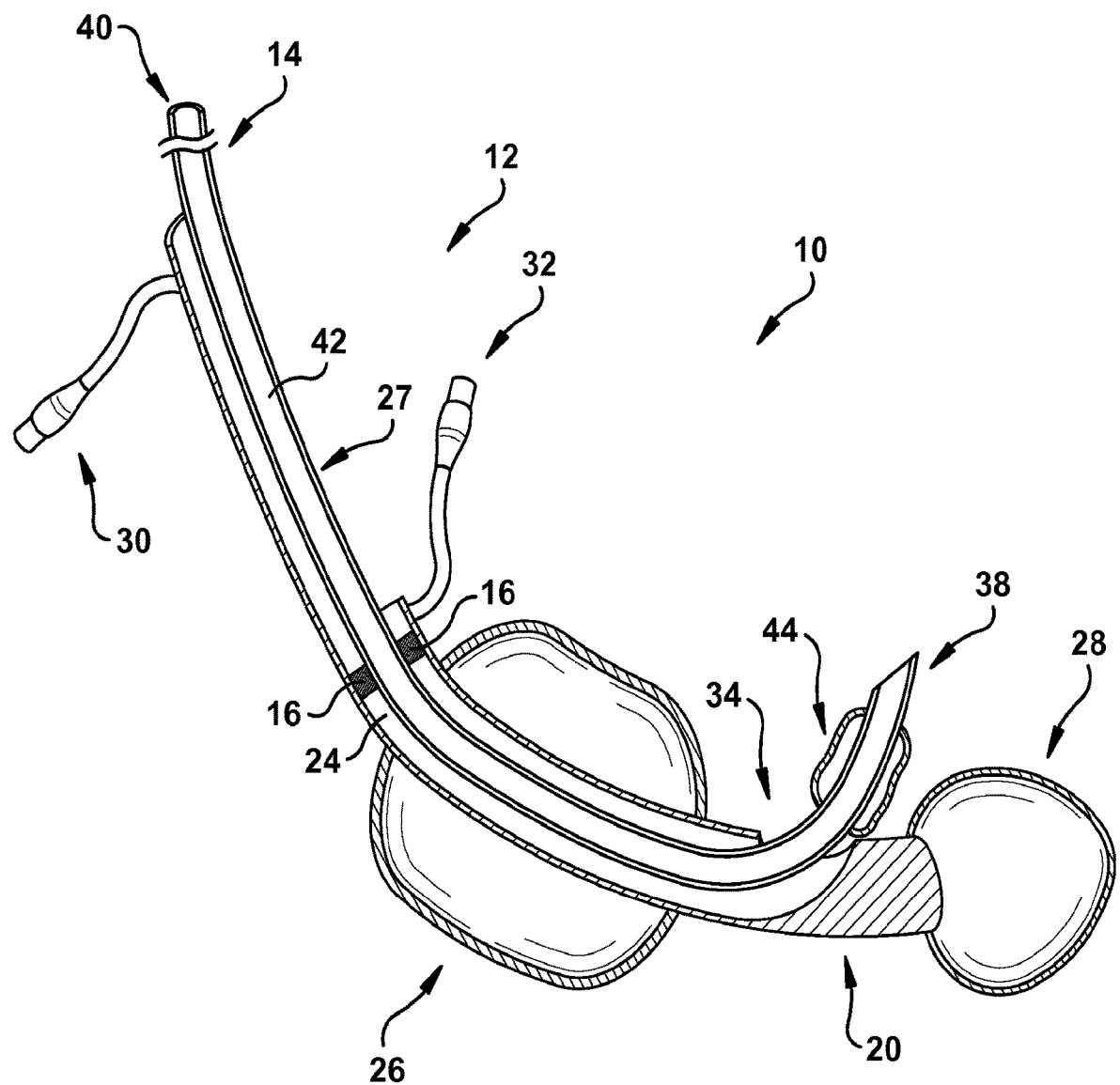
FIG. 2 is a cross-sectional view taken along Line 2-2 in FIG. 1.

As shown in FIG. 1, one component of the airway device 10 includes a supra-glottic airway support 12, such as a laryngeal tube. The supraglottic laryngeal tube 12 (or simply "laryngeal tube") can comprise a tubular guide 18 (e.g., a hollow tube) having a distal end portion 20, a proximal end portion 22, and a first passageway 24 (FIG. 2) that extends between the distal and proximal end portions. As discussed in more detail below, the first passageway 24 of the tubular guide 18 is sized and dimensioned to receive the endotracheal tube 14. When in use, the proximal end portion 22 of the tubular guide 18 remains outside of the subject's mouth and, therefore, is accessible to a healthcare provider (e.g., physician, nurse or other individual). The proximal end portion 22 of the tubular guide 18 may be conveniently of any size and shape to secure a variety of attachments (not shown) to the tubular guide (e.g., a syringe, an endoscope probe, a gas mix supply connection to receive a gas mix for ventilating, anesthetizing, etc., a patient, a drainage tube, etc.).

Figure 4:
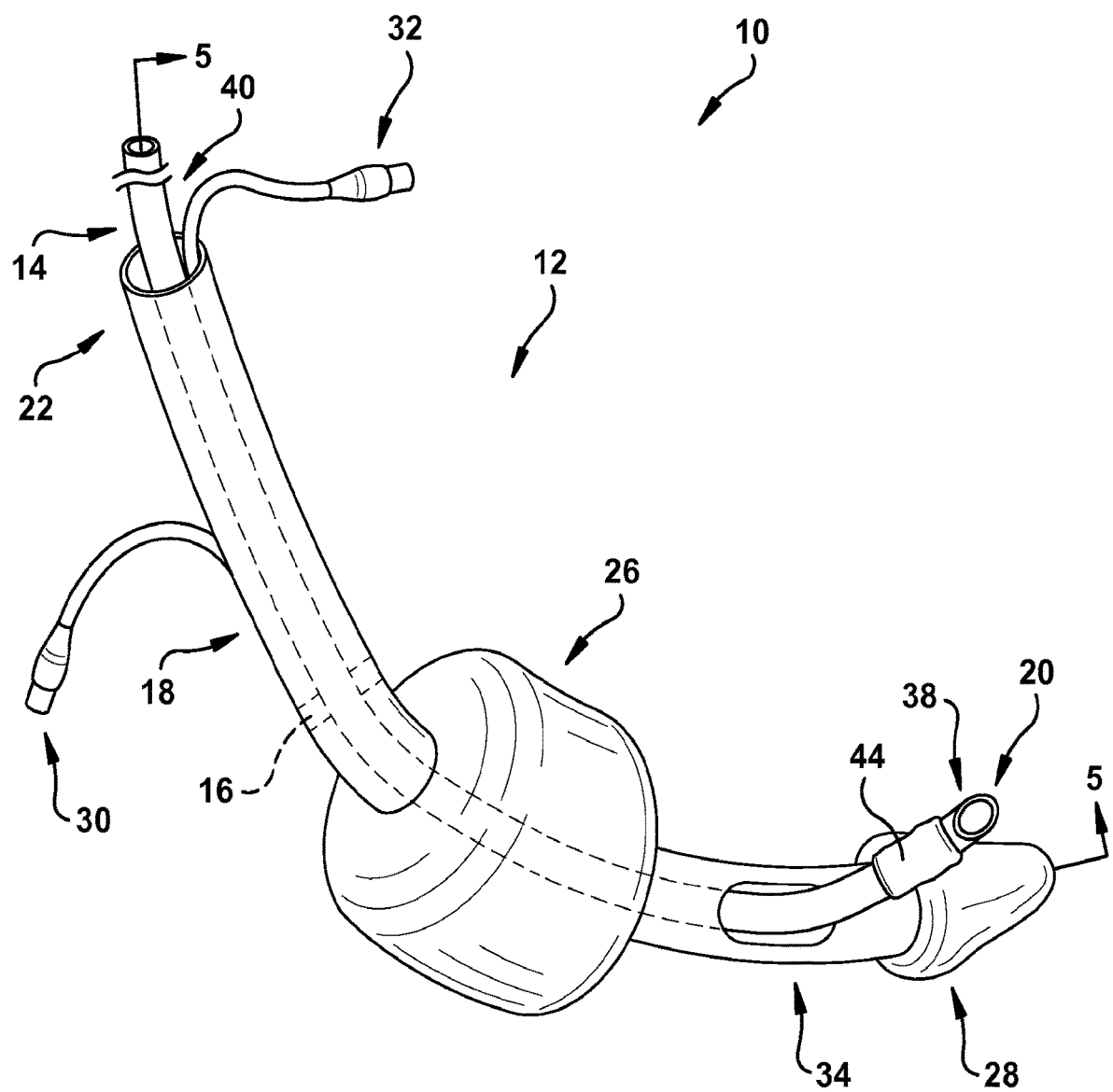
FIG. 4 is a perspective view of a reversible airway device constructed in accordance with another aspect of the present disclosure.
Figure 5:
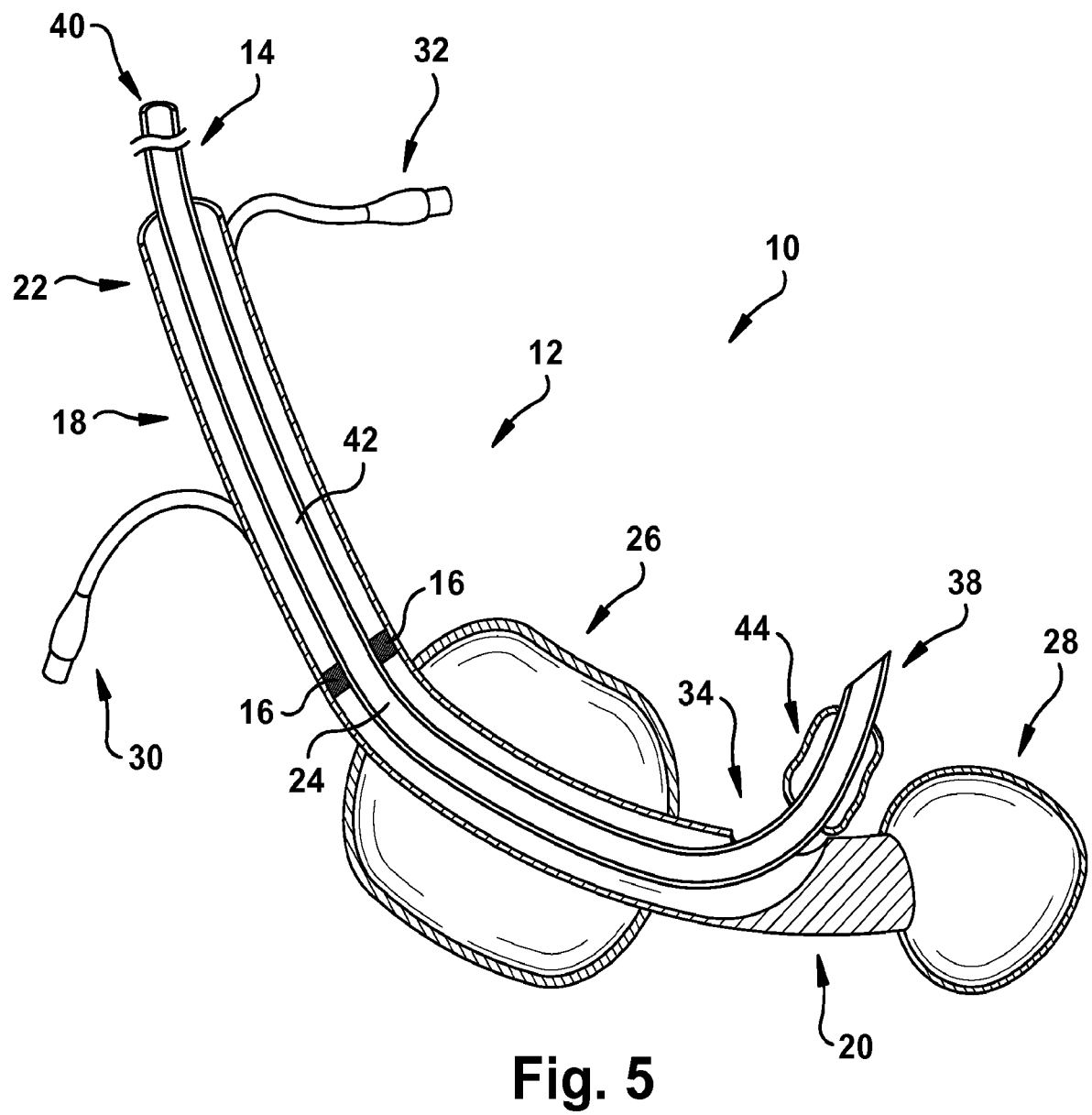
FIG. 5 is a cross-sectional view taken along Line 5-5 in FIG. 4.

As shown in FIG. 1, the laryngeal tube 12 can include a longitudinal slot 27 that partially extends between the distal and proximal end portions 20 and 22 of the tubular guide 18. The longitudinal slot 27 can serve as a rapid and convenient means for introducing the endotracheal tube 14 into the tubular guide 18. It will be appreciated that the longitudinal slot can be located on either the anterior or posterior portion of the tubular guide 18. Alternatively, as shown in FIGS. 4-5, the entire tubular guide 18 can have a tubular or cylindrical configuration. In other words, the tubular guide 18 can be free of a longitudinal slot 27.

Typically, the size and shape of the tubular guide 18 can be selected so that the distal end portion 20 can be readily inserted into a subject's mouth and upper airway. The tubular guide 18 is generally J-shaped to follow the profile of a typical subject's airway through the mouth, over the tongue, and into the laryngopharynx region of the subject. The tubular guide 18 can be made from one or a combination of materials, such as plastic, with sufficient strength and rigidity to keep the subject's teeth apart and to prevent the subject from biting down and collapsing the tubular guide. The tubular guide 18 can also be sized to accommodate a wide range of patient sizes (e.g., adult and pediatric patients).

As shown in FIG. 1, the tubular guide 18 further includes an inflatable proximal cuff 26 that is axially spaced apart from an inflatable distal cuff 28. Advantageously, the proximal cuff 26, when inflated, functions to hold the entire airway device 10 in place (i.e., in a patient's airway) during use. Consequently, this avoids slippage of the airway device 10 and potential loss of a patent airway. Although not shown in detail, first and second air valves 30 and 32 can be in fluid communication (e.g., via tubing) with each of proximal and distal cuffs 26 and 28, respectively. The proximal and distal cuffs 26 and 28 can be selectively inflated and deflated during use of the airway device 10. As discussed in more detail below, for example, the distal and proximal cuffs 28 and 26 can be inflated when the airway device 10 is inserted into the upper airway of a patient to form first and second airtight seals between the distal and proximal cuffs and the proximal esophagus and oropharynx of a subject (respectively). In some instances, the interior volume of the proximal cuff 26, when inflated, can be greater than the interior volume of the distal cuff 28 (when inflated). In other instances, the interior volume of the proximal cuff 26, when inflated, can be equal to, about equal to, or less than the interior volume of the distal cuff 28 (when inflated).

The distal end portion 20 of the tubular guide 18 can include an opening 34 in fluid communication with the first passageway 24. In some instances, the opening 34 can be beveled to substantially match the angle of the subject's laryngeal inlet after insertion of the airway device 10 into the subject's airway. In other instances, the laryngeal tube 12 can include a guide member 36 (FIG. 4B) for directing the endotracheal tube 14 at a desired angle (e.g., to substantially match the angle of the subject's laryngeal inlet). The guide member 36 can comprise a piece of plastic, for example, disposed on a surface of the laryngeal tube 12 adjacent the opening 34. In one example, the guide member 36 can have a rectangular shape and include a U-shaped cross-sectional profile. As shown in FIG. 4B, the guide member 36 can be disposed within the distal end portion 20 of the tubular guide 18 and extend partially outward therefrom. An angle $A_2$ formed by virtue of the guide member 36 can be customized depending upon the construction (e.g., length, width, thickness, etc.) of the guide member so that the angle $A_2$ is different from an angle $A_1$ (FIG. 4A), which is naturally formed by the bevel associated with the opening 34.

In another aspect, the airway device 10 includes an endotracheal tube 14 (FIG. 2) that is slidably disposed within the first passageway 24 of the tubular guide 18. By "slidably disposed", it is meant that the endotracheal tube 14 is not fixed within the first passageway 24 so that it is incapable of telescoping through the tubular guide 18. Rather, the term "slidably disposed" can mean that the endotracheal tube 14 is translatable along a longitudinal axis of the first passageway 24 (e.g., using tactile force). In some instances, substantially the entire length of the endotracheal tube 14 can extend through the first passageway 24. The endotracheal tube 14 can be sized and dimensioned to ventilate a patient requiring anesthesia and/or respiratory assistance. In some instances, the endotracheal tube 14 can comprise a plastic tube that can be passed through the laryngeal tube 12, past the vocal cords, and lodged in the trachea proximal (or above) the lungs. The endotracheal tube 14 can include a distal end 38, a proximal end 40, and a second passageway 42 that extends between the distal and proximal ends. Since the laryngeal tube 18 is sized and dimensioned to receive the endotracheal tube 14, a diameter associated with the first passageway 24 can be greater than a diameter associated with the second passageway 42. In some instances, when the endotracheal tube 14 is disposed in the first passageway 24, the second passageway 42 and the first passage way are concentric or coaxial with one another. In other instances, the first passageway 24 is not concentric with the second passageway 42 when the endotracheal tube 14 is disposed within the tubular guide 18. For example, where the tubular guide 18 has a non-circular cross-sectional profile (e.g., an oblong cross-sectional profile), the endotracheal tube 14 (and thus the second passageway 42) can be axially offset from, or non-concentric with, the first passageway 24.

The endotracheal tube 14 can include a cuff 44 or balloon portion surrounding the circumference of the endotracheal tube near the distal end 38 that rests in the patient's trachea. The cuff 38 can be inflated to seal against the wall of the trachea after the endotracheal tube 14 has been properly inserted into a subject. Once sealed, positive pressure ventilation may be used to provide respiratory assistance and, if desired, anesthesia or other gas, gas mix, etc., to the patient though the endotracheal tube 14 via a ventilator (not shown). The cuff 38 provides a seal that tends to block liquids and solids from passing along the outside of the endotracheal tube 14 between the tube and trachea wall and entering the patient's lungs. The endotracheal tube 14 can further include an inflation tube (not shown) and an air valve (not shown) for inflating and deflating the cuff 44.

In another aspect, the airway device 10 includes a sealing mechanism 16 (FIG. 3A) configured to occlude the flow of a gas, gas mix, etc., through the first passageway 24. The sealing mechanism 16 is disposed within a portion of the first passageway 24 (e.g., at any one or more points along the entire length of the tubular guide 18). The sealing mechanism 16 is configured to permit the endotracheal tube 14 to translate along the longitudinal axis of the tubular guide 18, while simultaneously preventing a gas, gas mix, etc., to flow between the distal and proximal end portions 20 and 22 of the tubular guide. The sealing mechanism 16 is configured to form a fluid-tight seal between an inner surface 46 (FIG. 3B) of the first passageway 24 and an outer surface 48 of the endotracheal tube 14. As discussed in more detail below, the sealing mechanism 16 (FIG. 3A) imparts the airway device 10 with the ability to change from the laryngeal tube 12 to an endotracheal tube 14 (and back again) by providing a single, common airway (i.e., the second passageway) that is not disrupted or stopped when the ventilation needs of the patient change.

Figure 3A:
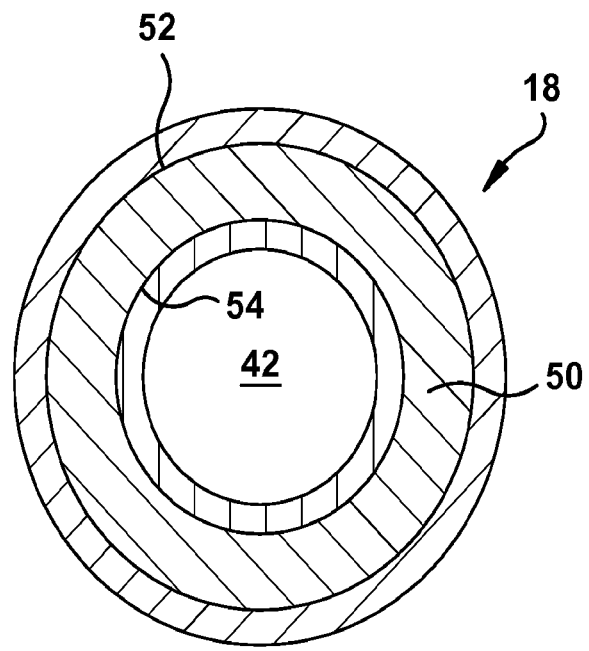
FIG. 3A is a cross-sectional view taken along Line 3A-3A in FIG. 1.
Figure 3B:
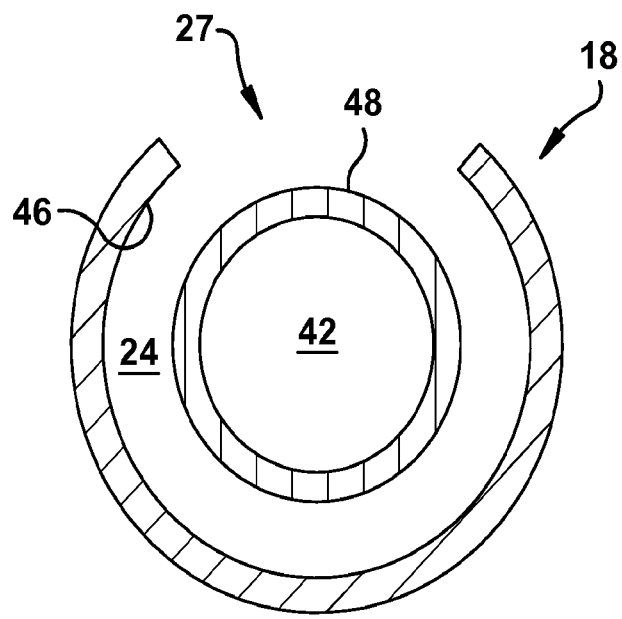
FIG. 3B is a cross-sectional view taken along Line 3B-3B in FIG. 1.

In some instances, the sealing mechanism 16 can include one or more sealing members 50 (FIG. 3A) configured to directly contact, and encircle, a portion of the outer surface 48 of the endotracheal tube 14. In one example, a sealing member 50 can include an O-ring, a gasket, an inflatable cuff or cushion, or the like. As shown in FIG. 3A, the sealing member 50 can comprise an O-ring having outer and inner circumferential surfaces 52 and 54 that are configured to directly contact the inner surface 46 of the first passageway 24 and the outer surface 48 of the endotracheal tube 14, respectively. By "directly contact", is meant that there are no intervening structures, components, elements, surfaces, etc., between a first structure or surface (e.g., the inner surface 46) and a second structure or surface (e.g., the outer surface 48). Although the sealing member 50 is shown and described as being located at the distal end portion 20 of the tubular guide 18, it will be appreciated that the sealing member can be located at any point within the tubular guide, such as at the proximal end portion 22. Additionally, it will be appreciated that two, three, or more sealing members 50 can be used to form the sealing mechanism 16.

Methods

Another aspect of the present disclosure includes a method 56 (FIG. 5) for providing an artificial airway in a subject. Although supra-glottic airway devices, such as laryngeal tubes, are known as rescue devices that are easy to use in less trained hands, such devices are not a definite airway. Current methods for changing a supra-glottic airway support device to an endotracheal tube involve using different devices; however, such methods risk the danger of disconnection and/or loss of the airway. As described below, the method 56 of the present disclosure advantageously provides a technique for maintaining the airway of a subject while changing between different forms of airway assistance. A high level of skill is not required to perform the method 56, which makes the present disclosure ideal for first responders, EMS personnel, etc., that may need to quickly change from a supra-glottic airway support device to an endotracheal tube (and back) without the requisite level of skill.

Figure 6A:
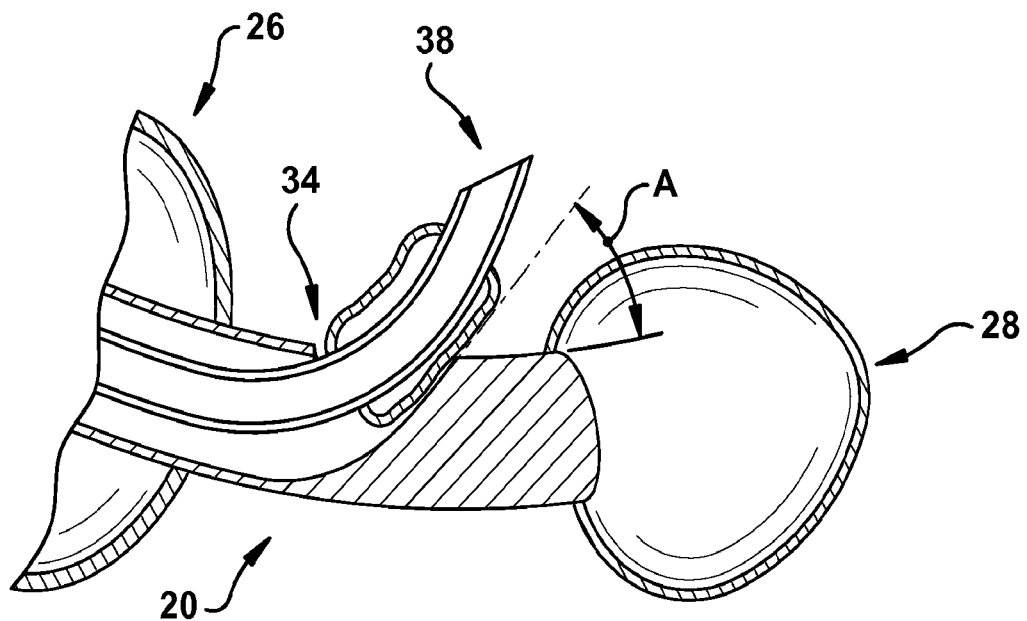
FIG. 6A is a cross-sectional view showing a distal end of the airway device in FIG. 1.
Figure 6B:
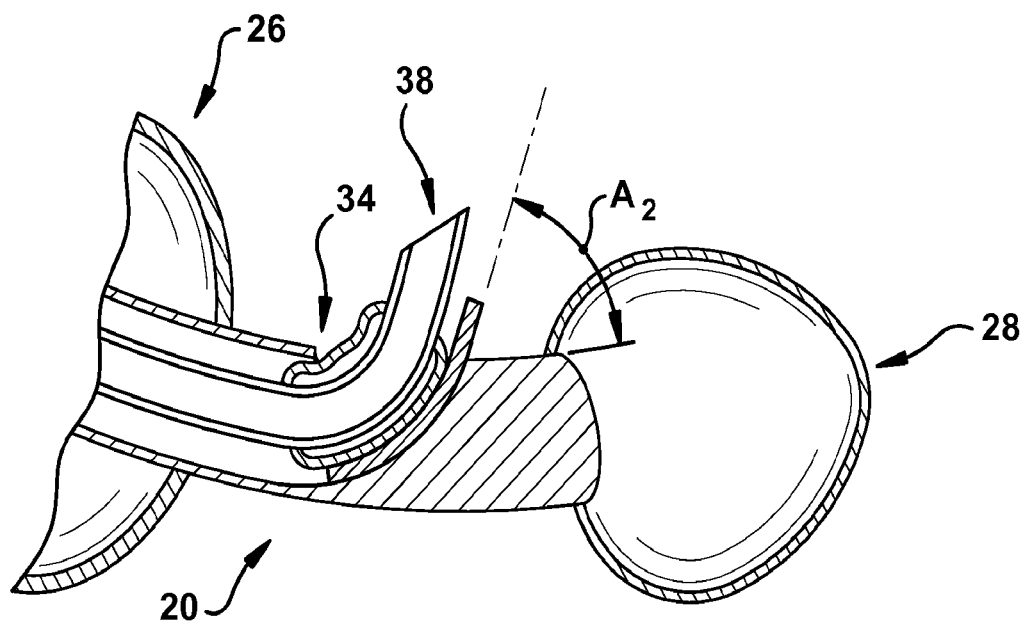
FIG. 6B is a cross-sectional view showing a guide member attached to the distal end of the airway device in FIG. 6A.
Figure 7:
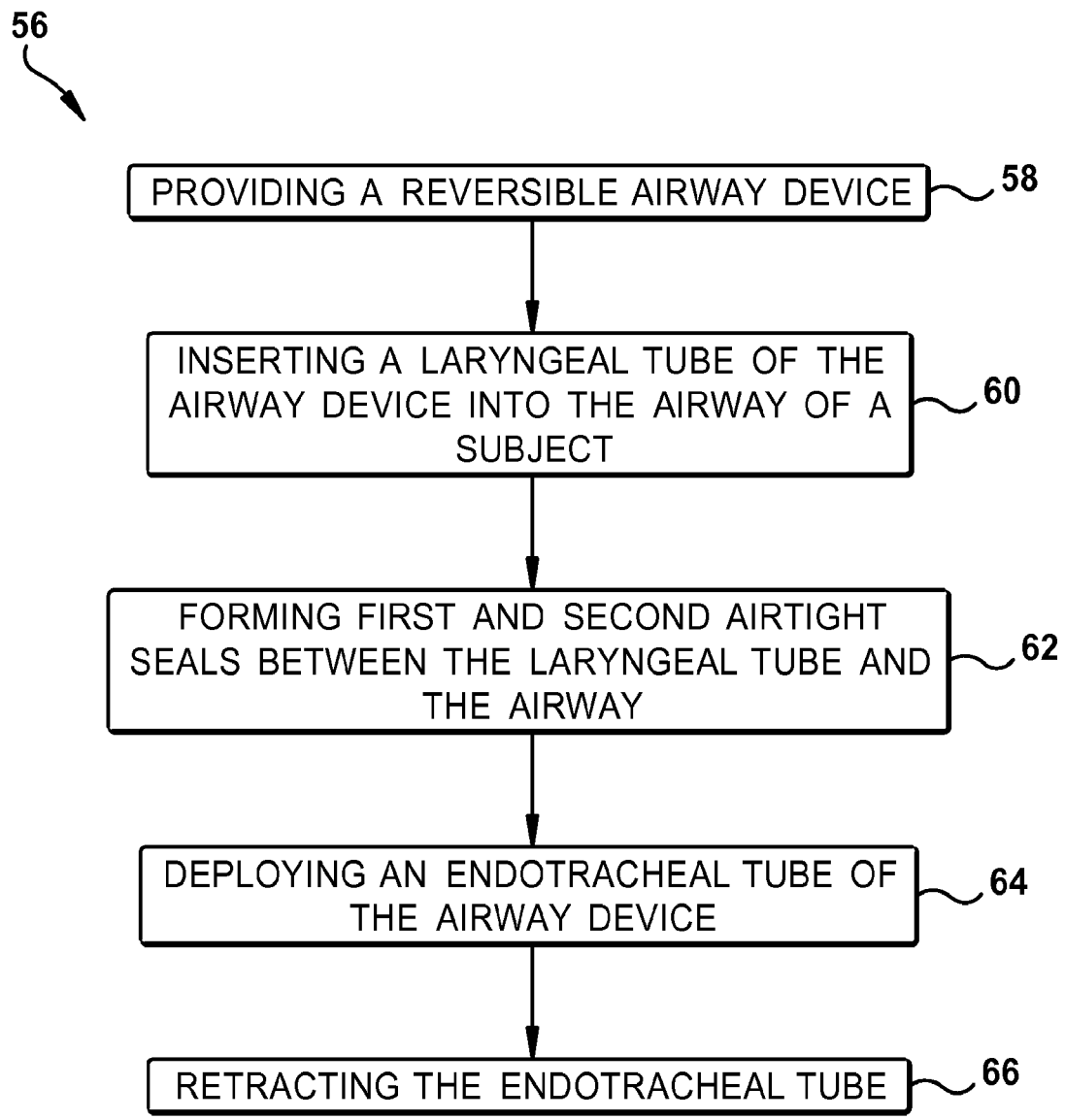
FIG. 7 is a process flow diagram illustrating a method for ventilating a subject according to another aspect of the present disclosure.
Figure 8:
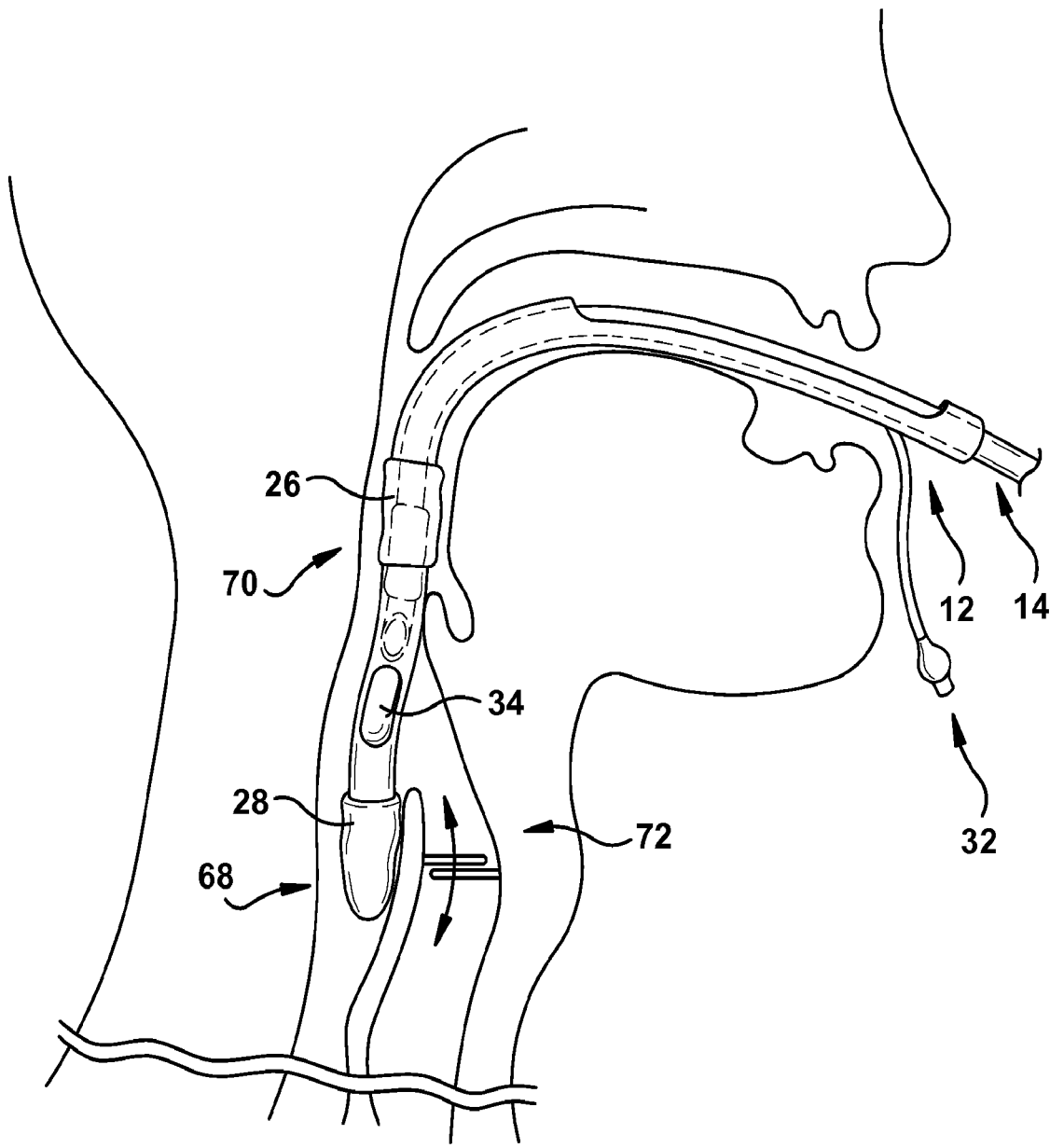
FIG. 8 is a schematic illustration showing the airway device in FIG. 1 inserted in the airway of a subject.
Figure 9:
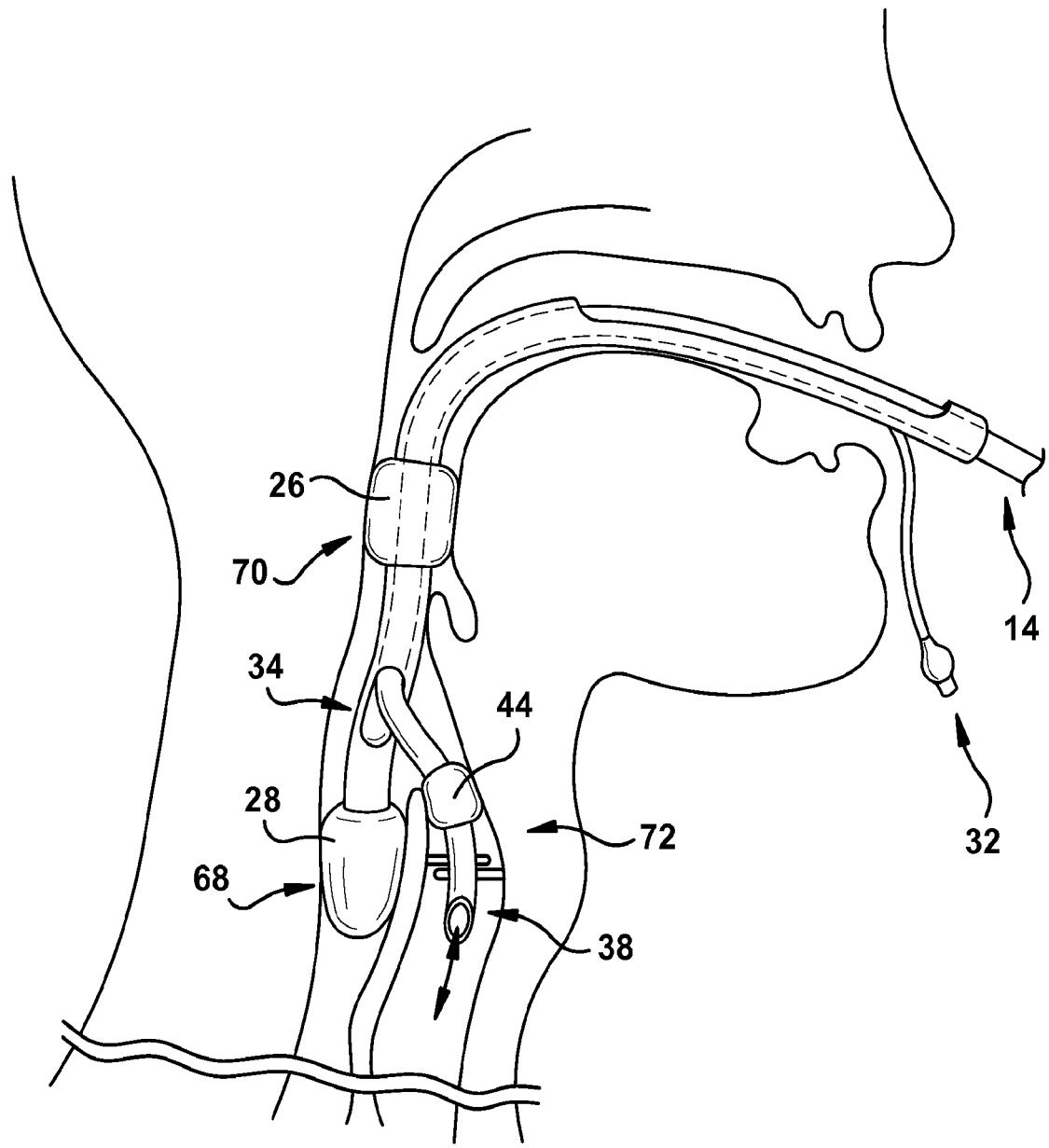
FIG. 9 is a schematic illustration showing an endotracheal tube of the airway device in FIG. 8 being deployed across the vocal cords of the subject.
Figure 10:
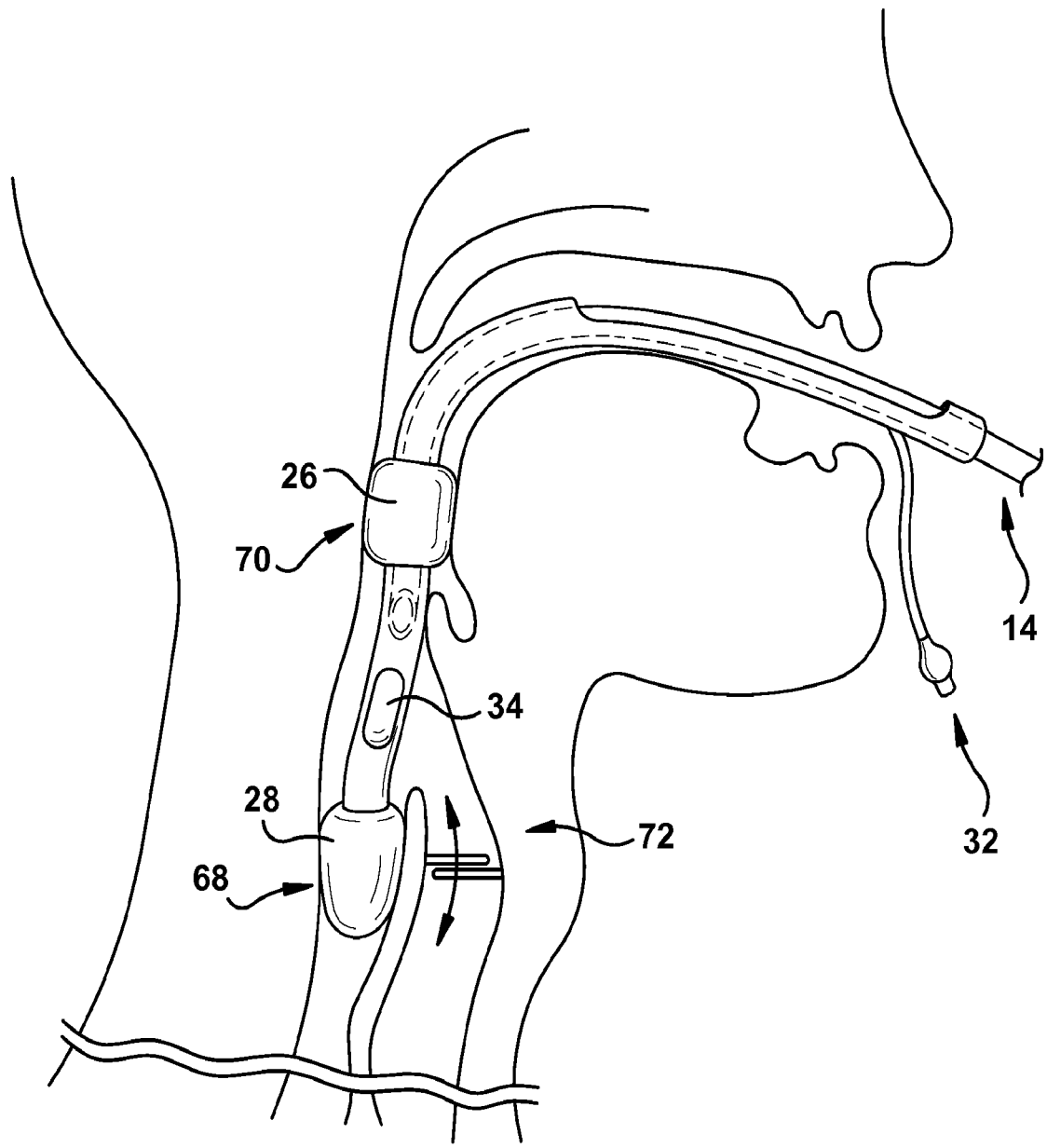
FIG. 10 is a schematic illustration showing the endotracheal tube in FIG. 9 being retracted from the trachea of the subject.

The method 56 can generally include the steps of providing a reversible airway device 10 (Step 58), inserting a laryngeal tube 12 of the airway device into a subject (Step 60), forming first and second airtight seals between the laryngeal tube and the airway (Step 62), deploying an endotracheal tube 14 of the airway device (Step 64), and retracting the endotracheal tube (Step 66). Referring to FIGS. 6-8, a patient is shown schematically with the mouth open in cross-section and leading to the back of the throat (sometimes the mouth and/or throat are referred to as the oral cavity of the patient), and from there to the trachea via the laryngeal inlet, which provides an airway that leads to the lungs.

At Step 58, the method 56 can include providing a reversible airway device 10. The reversible airway device 10 can be constructed in an identical or similar manner as shown in FIG. 1 and described above. It will be appreciated that the airway device 10 can be sized and dimensioned to accommodate a variety of patient sizes, such as adult or pediatric patients.

After selecting an appropriately-sized airway device 10, the laryngeal tube 12 can be inserted into the oral cavity (mouth) of the subject (Step 60). The laryngeal tube 12 can be inserted using, for example, fiberoptic visualization or other form(s) of facilitated visualization modality to assist in confirming passage of the endotracheal tube 14. Alternatively, the laryngeal tube 12 can be inserted under direct visualization; that is, without the use or aid of any facilitated visualization modality (or modalities). As shown in FIG. 6, the laryngeal tube 12 can be positioned so that the distal cuff 28 extends into the proximal esophagus 68 and the proximal cuff 26 is situated in the oropharynx 70 of the patient. Once inserted, the distal and proximal cuffs 28 and 26 can be inflated to form first and second airtight seals, respectively (Step 62) (FIG. 7). The first seal can substantially block the proximal esophagus 68 to minimize the risk of regurgitation of stomach contents and the passage of air into the stomach. The second seal can substantially prevent air from escaping or entering the airway. Thus, substantially all of the gas inhaled or exhaled by the patient passes through the second passageway 42 of the endotracheal tube 14.

The endotracheal tube 14 of the airway device 10 can then be deployed, if necessary, at Step 64. The endotracheal tube 14 can be deployed automatically or under direct fiberoptic view (or other methods) or without fiberoptic assistance. In some instances, ventilation can continue during fiberoptic or other placement by an adaptor (not shown) that is configured to mate with the fiberoptic visualization tool during ventilation. As shown in FIG. 7, the proximal end 40 of the endotracheal tube 14 can be urged downward through the tubular guide 18 using, for example, tactile force. As the endotracheal tube 14 is advanced, the distal end 38 emerges from the opening 34 of the laryngeal tube 12 and passes through the vocal cords 72 of the patient until the cuff 44 of the endotracheal tube is positioned distal (below) the vocal cords. Next, the cuff 44 of the endotracheal tube 14 can be inflated to seal against the wall of the trachea. Once sealed, positive pressure ventilation may be used to provide respiratory assistance and, if desired, anesthesia or other gas, gas mix, etc., to the patient though the second passageway 42 of the endotracheal tube 14 via a ventilator.

When intubation with the endotracheal tube 14 is no longer necessary, the cuff 44 can be deflated and the distal end 38 withdrawn into the tubular guide 18 as shown in FIG. 8 (Step 66). Since an airtight seal is still maintained between the proximal cuff 26 and the oropharynx 70, ventilation of the patient can continue uninterrupted through the second passageway 42 upon discontinuing ventilation with the endotracheal tube 14. Alternatively, if there is a failure of intubation using the endotracheal tube 14, the airway device 10 can be changed to the laryngeal tube 12 without compromising ventilation since the first and second seals are maintained. Advantageously, the laryngeal tube 12 can thus be extracted from the patient or kept in situ for later use.

From the above description of the present disclosure, those skilled in the art will perceive improvements, changes and modifications. For example, it will be appreciated that order of steps can be changed so that the endotracheal tube 14 is deployed before Step 60 of the method 56. Such improvements, changes, and modifications are within the skill of those in the art and are intended to be covered by the appended claims. All patents, patent applications, and publication cited herein are incorporated by reference in their entirety.

The following is claimed:

1. A reversible airway device for ventilating a subject, the airway device comprising:
    a laryngeal tube including a tubular guide having a distal end portion, a proximal end portion, and a first passageway extending between the distal and proximal end portions, the laryngeal tube further including axially spaced apart distal and proximal inflatable cuffs coupled thereto;
    an endotracheal tube slidably disposed within the first passageway, the endotracheal tube having a second passageway that is disposed within the first passageway; and
    a sealing mechanism disposed within the first passageway and being configured to occlude the flow of gas through the first passageway, wherein the sealing mechanism is disposed proximate a longitudinal slot that extends partially between the distal end portion and the proximal end portion of the tubular guide.

2. The airway device of claim 1, wherein the distal end portion of the laryngeal tube includes an opening in fluid communication with the first passageway and through which a portion of the endotracheal tube is deployed.

3. The airway device of claim 2, wherein the laryngeal tube includes a guide member for directing the endotracheal tube at a desired angle when the endotracheal tube is urged through the opening.

4. The airway device of claim 1, wherein a majority of the length of the endotracheal tube is disposed in, and extends through, the first passageway.

5. The airway device of claim 1, wherein a diameter associated with the first passageway is larger than a diameter associated with the second passageway.

6. The airway device of claim 1, wherein at least one of the first and second passageways is flexible.

7. The airway device of claim 1, wherein the sealing mechanism includes one or more sealing members that encircle the endotracheal tube and ensure that a gas only flows through the second passageway.

8. The airway device of claim 1, wherein the second passageway of the endotracheal tube is concentric with the first passageway of the laryngeal tube.

9. The airway device of claim 1, wherein the second passageway of the endotracheal tube is not concentric with the first passageway of the laryngeal tube.

10. A reversible airway device for ventilating a subject, the airway device comprising:
    a laryngeal tube including a tubular guide having a distal end portion, a proximal end portion, and a first passageway extending between the distal and proximal end portions, the laryngeal tube further including axially spaced apart distal and proximal inflatable cuffs coupled thereto;
    an endotracheal tube slidably disposed within the first passageway, the endotracheal tube having a second passageway that is concentric with the first passageway; and
    a sealing mechanism disposed within the first passageway and being configured to occlude the flow of gas through the first passageway, wherein the sealing mechanism is disposed proximate a longitudinal slot that extends partially between the distal end portion and the proximal end portion of the tubular guide.

11. The airway device of claim 10, wherein the distal end portion of the laryngeal tube includes an opening in fluid communication with the first passageway and through which a portion of the endotracheal tube is deployed.

12. The airway device of claim 11, wherein the laryngeal tube includes a guide member for directing the endotracheal tube at a desired angle when the endotracheal tube is urged through the opening.

13. The airway device of claim 10, wherein a majority of the length of the endotracheal tube is disposed in, and extends through, the first passageway.

14. The airway device of claim 10, wherein a diameter associated with the first passageway is larger than a diameter associated with the second passageway.

15. The airway device of claim 10, wherein the sealing mechanism includes one or more sealing members that encircle the endotracheal tube and ensure that a gas only flows through the second passageway.

16. A reversible airway device for ventilating a subject, the airway device comprising:
    a laryngeal tube including a tubular guide having a distal end portion, a proximal end portion, and a first passageway extending between the distal and proximal end portions, the laryngeal tube further including axially spaced apart distal and proximal inflatable cuffs coupled thereto;
    an endotracheal tube slidably disposed within the first passageway, the endotracheal tube having a second passageway that is not concentric with the first passageway; and
    a sealing mechanism disposed within the first passageway and being configured to occlude the flow of gas through the first passageway, wherein the sealing mechanism is disposed proximate a longitudinal slot that extends partially between the distal end portion and the proximal end portion of the tubular guide.

17. The airway device of claim 16, wherein the laryngeal tube includes a guide member for directing the endotracheal tube at a desired angle when the endotracheal tube is urged through an opening provided on the distal end portion of the laryngeal tube.

18. The airway device of claim 16, wherein a majority of the length of the endotracheal tube is disposed in, and extends through, the first passageway.

19. The airway device of claim 16, wherein a diameter associated with the first passageway is larger than a diameter associated with the second passageway.

20. The airway device of claim 16, wherein the sealing mechanism includes one or more sealing members that encircle the endotracheal tube and ensure that a gas only flows through the second passageway.

\* \* \* \* \*